US006281199B1

(12) United States Patent
Gupta

(10) Patent No.: US 6,281,199 B1
(45) Date of Patent: Aug. 28, 2001

(54) **METHOD OF TREATMENT OF HEART DISEASE CAUSED BY *CHLAMYDIA PNEUMONIAE***

(75) Inventor: Sandeep Gupta, London (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/294,013

(22) Filed: Apr. 19, 1999

Related U.S. Application Data

(63) Continuation of application No. PCT/GB97/02862, filed on Oct. 17, 1997.
(60) Provisional application No. 60/028,693, filed on Oct. 18, 1996.

(30) Foreign Application Priority Data

Oct. 18, 1996 (GB) .................................................. 9621771

(51) Int. Cl.$^7$ .......................... A61K 31/70; A61K 31/395
(52) U.S. Cl. .............................................. 514/29; 514/210
(58) Field of Search ........................................ 514/29, 210

(56) References Cited

U.S. PATENT DOCUMENTS

| 4,427,782 | 1/1984 | Caldwell et al. | 436/542 |
|---|---|---|---|
| 5,424,187 | 6/1995 | Shor et al. | 435/6 |
| 5,830,874 | * 11/1998 | Shor et al. | 514/29 |

FOREIGN PATENT DOCUMENTS

| 192033 | 8/1986 | (EP) . |
|---|---|---|
| WO 90/00061 | 1/1990 | (WO) . |
| WO 92/22819 | 12/1992 | (WO) . |

OTHER PUBLICATIONS

Proc. Natl. Acad. Sci. USA; Kuo et al; *Chlamydia pneumoniae* (TWAR) in coronary arteries in young adults (15–34 years old); 1995; 92:6911–6914.

The Journal of Infectious Diseases; Weiss et al; Failure to detect *chlamydia penumoniae* in coronary atheromas of patients undergoing atherectomy; 1996; 173:957–62.

JACC; Muhlenstein et al; Increased incidence of chlamydia species within the coronary arteries of patients with symptomatic atherosclerotic versus other forms of cardiovascular disease; 1996; 27(7):1555–61.

The Lancet; Saikku et al; Serological evidence of an association of a novel chlamydia, TWAR, with chronic coronary heart disease and acute myocardial infarction; 1988; 983–985.

Transplantation Proceedings; Virella et al; Infections and atherosclerosis; 1987; vol. XIX, No. 4, Suppl 5:26–35.

Journal of Infection; Bromage et al; Embolic phenomena in chlamydial infection; 1980; 2:151–159.

Clinical Immunology and Immunopathology; Lopes–Virella et al; 1985; 37:377–386.

Heart; Niemelä et al; Could *helicobacter pylori* infection increase the risk of coronary heart disease by modifying serum lipid concentrations?; 1996; 75:573–575.

J. Clin. Lab. Immunol; Smith et al; Circulating immune complexes in myocardial infarction; 1983; 12:197–199.

The New England Journal of Medicine; Grayston et al; 1986; vol. 315, No. 3:161–168.

Immunology Letters; Cristea et al; Characterization of circulating immune complexes in heart disease; 1986; 13:45–49.

Atherosclerosis; Füst et al; Studies on the occurrence of circulating immune complexes in vascular diseases; 1978; 29:181–190.

Scand. J. Immunol; Farrell et al; A survey for circulating immune complexes in patients with acute myocardial infarction; 1977; 6:1233–1240.

Sutton et al; Pericardial and myocardial disease with serological evidence of infection by agents of the psittacosis–*lymphogranuloma venereum* group (chlamydiaceae); 1967; vol. XXXVI:830–838.

American Heart Journal; Sutton et al; Serologic evidence of a sporadic outbreak in Illinois of infection by chlamydia (psittacosis–*LGV* agent) in patients with primary myocardial disease and respiratory disease; 1971; vol. 81, No. 5:597–607.

The British Journal of Clinical Practice; Dymock et al; Myocarditis associated with psittacosis; 1971; vol. 25, No. 5:240–242.

C Trachomatis Myocarditis; Grayston et al; Childhood myocarditis associated with *chlamydia trachomatis* infection; 1981; vol. 246, No. 24:2823–2827.

Br. Heart J.; Walker et al; Successful treatment by doxycycline of endocarditis caused by ornithosis; 1987; 57:58–60.

Pediatrics; Ringel et al; Serologic evidence for *chlamydia trachomatis* myocarditis; 1982; vol. 70, No. 1:54–56.

Antimicrobial Agents and Chemotherapy; Kuo et al; In vitro drug susceptibility of Chlamydia sp. strain TWAR; 1988; 257–258.

Br. Heart J.; Svendsen et al; Combined pericarditis and pneumonia caused by Legionella infection; 1987; 58:663–4.

Israel Journal of Medical Sciences; Isakov et al; Legionnaires' disease: a case acquired in Israel; 1982; 18:873–877.

European Heart Journal; Ribeiro et al; Pericarditis in infective endocarditis; 1985; 6:975–978.

(List continued on next page.)

Primary Examiner—Frederick Krass
Assistant Examiner—Donna Jagoe
(74) Attorney, Agent, or Firm—Bacon & Thomas

(57) ABSTRACT

A method of combatting atherosclerosis by administering an effective amount of a macrolide antibiotic, for example an azalide such as azithromycin, optionally together with one or more pharmaceutically acceptable carriers or excipients, to a subject.

4 Claims, No Drawings

OTHER PUBLICATIONS (Abstract) Antimicrobial agents and chemotherapy; Agacfidan et al; In vitro activity of azithromycin (CP–62,993) against *Chlamydia trachomatis* and *Chlamydia pneumoniae;* 1993; 37:1746–1748.

(Abstract) La Presse Medical; Bruaire et al; Pneumopathies caused by *Chlamydia pneumoniae;* 1992; 21:1064–1069.

(Abstract) Antimicrobial Agents and Chemotherapy; Chirgwin et al; In vitro susceptibilities of *Chlamydia pneumonia* (Chlamydia sp. strain TWAR); 1989; 33:1634–1635.

(Abstract) Journal of Antimicrobial Chemotherapy; Cooper et al; In vitro susceptibility of *Chlamydia pneumoniae* (TWAR) to seven antibiotics; 1991; 28:407–413.

(Abstract) 9th Mediterranean Congress of Chemotherapy, Milan, Italy, Jun. 12–17; Cosentini et al; *Chlamydia pneumoniae:* role of new macrolides; 1994; Abstract No. 009.

(Abstract) Journal of Antimicrobial Chemotherapy: Fenelon et al; The in vitro antibiotic susceptibility of *Chlamydia pneumoniae;* 1990; 26:763–767.

(Abstract) Clinical Infectious Diseases; Grayston; Infections caused by *Chlamydia pneumoniae* strain TWAR; 1992; 15:757–763.

(Abstract) Journal of Family Practice; Hahn; Treatment of *Chlamydia penumoniae* infection in adult asthma: a before–after trial; 1995; 41:345–351.

(Abstract) In the New Macrolides, Azalides and Streptogramins: Pharmacology and Clinical Applications. Eds New H C, Young L S, Zinner S H; Hammerschlag; Infections due to *Mycoplasma pneumoniae* and *Chlamydia pneumoniae;* 1993; 137–140.

(Abstract) Antimicrobial Agents and Chemotherapy; Hammerschlag et al; In vitro activities of azithromycin, clarithromycin, L–ofloxacin, and other antibiotics against *Chlamydia pneumoniae;* 1992; 36:1573–1574.

(Abstract) Presented at: 7th European Congress for Clinical Microbiology and Infectious Diseases, Mar. 26–30, 1995; Pechere: Impact of azithromycin and newer macrolides in the management of community–acquired pneumonia; 1995; Abstract No. 20.

(Abstract) The Practitioner; Ridgway; TWAR and changing respiratory infections; 1990; 234:790–792.

(Abstract) Journal of Antimicrobial Chemotherapy; Ridgway et al; The in vitro activity of clarithromycin and other macrolides against *Chlamydia pneumoniae* (TWAR): 1991; 27(Suppl. A):43–45.

Abstract) European Respiratory Journal; Rizzato et al; Efficacy of a three–day course of azithromycin in moderately severe community–acquired pneumonia; 1995; 8:398–402.

(Abstract) Program and Abstracts of the 35th Interscience Conference on Antimicrobial Agents and Chemotherapy, San Francisco, California, USA, Sep. 17–20, 1995; Roblin et al; Susceptibilities of azithromycin of isolates of *Chlamydia pneumoniae* from patients with community acquired pneumonia; 1995; Abstract No. E44:93.

(Abstract) Journal of the Formosan Medical Association; Wang et al; Azithromycin in the treatment of pneumonia caused by *Chlamydia pneumoniae:* report of a case; 1994; 93:642–4.

(Abstract) Antimicrobial Agents and Chemotherapy; Welsh et al; In vitro activities of azithromycin, clarithromycin, erythromycin, and tetracycline against 13 strains of *Chlamydia pneumoniae;* 1996; 40:212–214.

(Abstract) J–Clin–Pathol; Ong et al; Detection and widespread distribution of *chlamydia pneumoniae* in the vascular system and its possible implications; 1996; vol. 49(2):102–6.

(Abstract) Microb–Pathog; Kaukoranta–Tolvanen et al; *Chlamydia pneumoniae* multiples in human endothelial cells in vitro; 16/4:313–319.

(Abstract) J–Infect; Mendall et al; *Chlamydia pneumoniae:* risk factors for seropositivity and association with coronary heart disease; 1995; 30(2):121–8.

(Abstract) Acupunct–Electrother–Res; Omura; Treatment of acute or chronic severe, intractable pain medical problems associates with unrecognized viral or; 1990; 15(1):51–69.

Int–J–STD–AIDS; Wilson et al; Infection with Chlamydia sp and HTLV–I in a patient mimicking infective endocarditis; 1990; 1(3):213–5.

(Abstract) Microb–Pathog; Leinonen et al; Circulating immune complexes containing chlamydial lipopolysaccharide in acute myocardial infarction; 1990; 9(1):67–73.

(Abstract) Nippon–Kyobu–Shikkan–Gakkai–Zasshi; Hayashi et al; [A case report of psittacosis and chlamydial isolation from a dead pet bird]; 1990; 28(3):535–40.

(Abstract) J–Infect–Dis; Campbell et al; Detection of *Chlamydia pneumoniae* TWAR in human coronary atherectomy tissues; 1995; 172(2):585–8.

(Abstract) Am–J–Pathol; Moazed et al; Experimental rabbit models of *chlamydia pneumoniae* infection; 1996; vol. 148(2):667–76.

Baillieres–Clin–Haematol; Hershko; Control of disease by selective iron depletion: a novel therapeutic strategy utilizing iron chelators; 1994; 7(4):965–1000.

Duodecim; Mattila et al; [Infections and coronary heart disease]; 1991; 107(15):1269–74.

(Abstract) Rev–Prat; Capron et al; [The past, present and future of arterial infection]; 1994; 44(7):906–10.

Lancet; Patel et al; Fibrinogen: a link between chronic infection and coronary heart disease; 1994; 343(8913):1634–5.

Lakartidningen; Persson; [TWAR and heart disease. A questionable connection]; 1994, 91(8):708–10, 715.

(Abstract) Vet–Pathol; Homer et al; Chlamydiosis in mariculture–reared green sea turtles; 1994; 31(1):1–7.

(Abstract) Eur–Heart–J.; Saikku; *Chlamydia pneumoniae* infection as a risk factor in acute myocardial infarction; 1993; 14 Suppl K:62–5.

(Abstract) Eur–Heart–J; Nieminen et al; Infection and inflammation as risk factors for myocardial infarction; 1993; 14 Suppl K: 12–6.

(Abstract) Am–J–Med; Melnick et al; Past infection by *Chlamydia pneumoniae* strain TWAR and asymptomatic carotid atherosclerosis: Atherosclerosis Risk in Communities (ARIC) Study Investigators; 1993; 95(5):499–504.

J–Clin–Epidemiol; Hahn; Regional variation in ischemic heart disease: a possible missing risk factor?; 1993; 46(7):668–9.

(Abstract) Circulation; Linnanmaki et al; *Chlamydia pneumoniae*–specific circulating immune complexes in patients with chronic coronary heart disease; 1993; 87(4):1130–4.

(Abstract) Tidsskr–Nor–Laegeforen; Berdal et al; [*Chlamydia pneumoniae*pathogenesis and perspectives]; 1993; 113(7): 859–61.

Lakartidningen; Wilhemson; [The "orienteering disease"—more cases discovered. A new type of myocarditis behind sudden death?]; 1993; 90(9):772–81.

Lancet; Wesslen et al; Myocarditis caused by *Chlamydia pneumoniae* (TWAR) and sudden unexpected death in a Swedish elite orienteer; 1992; 340(8816):427–8.
(Abstract) Eur–J–Clin–Microbiol–Infect–Dis; Odeh et al; Chlamydial infections of the heart; 1992; 11(10):885–93.
(Abstract) Eur–Heart–J; Etienne et al; Chlamydial endocarditis: a report on ten cases; 1992; 13(10):1422–6.
(Abstract) J–Infect; Saikku; The epidemiology and significance of *Chlamydia pneumoniae*; 1992; 25 Suppl 1: 27–34.
(Abstract) Zentralbl–Pathol; Manghani et al; The lung in tropical eosinophilia compared to that in pulmonary hypertension. Fine structural basis of respiratory disability; 1992; 138(2):108–18.
(Abstract) JAMA; Thom et al; Association of prior infection with *Chlamydia pneumoniae* and angiographically demonstrated coronary artery disease; 1992; 268(1):68–72.
Ann–Intern–Med; Hahn; Chlamydia, smoking, and heart disease [letter; comment]; 1992; 117(2):171.
(Abstract) Ann–Intern–Med; Saikku et al; Chronic *Chlamydia pneumonia* infection as a risk factor for coronary heart disease in the Helsinki Heart Study [see comments]; 1992; 116(4):273–8.
(Abstract) Respiration; Pacheco et al; Community acquired pneumonia caused by *Chlamydia pneumoniae* strain TWAR in chronic cardiopulmonary disease in the elderly; 1991; 58(5–6):316–20.
(Abstract) Ann–Med; Valtonen; Infection as a risk factor for infarction and atherosclerosis; 1991; 23(5):539–43.
(Abstract) Arterioscler–Throm; Thom et al; *Chlamydia pneumoniae* strain TWAR antibody and angiographically demonstrated coronary artery disease; 1991; 11(3):547–51.
(Abstract) Arch–Fr–Pediatr; Benoit et al; [QT prolongation and circulatory arrest after an injection of erythromycin in a newborn infant]; 1991; 48(1):39–41.
(Abstract) J–Intern–Med; Odeh et al; Dilated cardiomyopathy associated with *Chlamydia trachomatis* infection; 1991; 229(3):2898–91.
(Abstract) J–Wild–Dis; Mirande et al; Chlamydiosis in red–tailed hawk; 1992; 28(2):284–7.
(Abstract) BMJ; Patel et al; Association of *Helicobacter pylori* and *chlamydia pneumoniae* infections with coronary heart disease and cardiovascular risk factors (see comments); 1995; VO1 311(7007):711–4.
(Abstract) Atherosclerosis; Dhalen et al; Lp(a) lipoprotein, IgG, IgA and IgM antibodies to *chlamydia pneumoniae* and HLA class II genotype in early coronary artery disease; 1995; vol. 114(2):165–74.
(Abstract) Eur–Heart–J; Grayston et al; *Chlamydia pneumoniae*, strain TWAR and atherosclerosis; 1993; vol. 14 Supple K:66–71.
(Abstract) Arterioscler–Thromb; Kuo et al; Detection of *chlamydia pneumoniae* in aortic lesions of atherosclerosis by immunocytochemical stain; 1993; vol. 13(10):1501–4.
(Abstract) J–Clin–Microbiol; Puolakkainen et al; Serological response to *chlamydia pneumoniae* in adults with coronary arterial fatty streaks and fibrolipid plaques; 1993; vol. 31(8); 2212–4.
(Abstract) J–Infect–Dis; Kuo et al; Demonstration of *chlamydia pneumoniae* in atherosclerotic lesions of coronary arteries; 1993; vol. 167(4):841–9.
(Abstract) S–Afr–Med–J; Shor et al; Detection of *chlamydia pneumoniae* in coronary arterial fatty streaks and atheromatous plaques; 1992; vol. 82(3):158–61.
(Abstract) Arterioscler–Thromb; Hahn et al; Smoking is a potential confounder of the *chlamydia pneumoniae*–coronary artery disease association; 1992; vol. 12(8):945–7.
Marrie: "*Chlamydia pneumoniae*", *Thorax*, vol. 48, No. 1, 1993, pp. 1–4.
Cook: "*Chlamydia pneumoniae*" *J. Antimicrob. Chemotherapy*, vol. 34, No. 6, 1994, pp. 859–873.
Cook: "Clinical Aspects of *Chlamydia Pneumoniae* Infection" *La Presse Medicale*, vol. 24, No. 5, 1995, pp. 278–282.
Valtonen: "Symposium Graft Infection Sponsored by the Sanofi–Chinoin Co.: The Causative Role of *Chlamydia Pneumoniae* and Other Bacteria in the Development of Coronary Heart Disease" *International Angiology*, vol. 15, No. 2, suppl. May, 1996, p. 61.
Stille: "Argumente für eine Antibiotika–Therapie der Atherosklerose" *Chemother. J.*, vol. 6, No. 1, 1997, pp. 1–5.
Blanchard: "Chlamydia Infections" *Br. J. Clin. Pract.*, vol. 48, No. 4, 1994, pp. 201–205.
Gaydos: "*Chlamydia Pneumoniae*: A Review and Evidence for a Role in Coronary Artery Disease" *Clinical Microbiology Newsletter*, vol. 17, No. 7, 1995, pp. 49–54.
R.W. Wissler, Circulation, 92, p. 33376, 1995.
R. Malinverni et al., Antimicrobial Agents and Chemotherapy, vol. 39, pp. 45–49, Jan. 1995.
J. T. Grayston et al., Circulation, vol. 92, pp. 3397–340, Dec. 15, 1995.
(Abstract) S. Gupta et al., XVIIIth Congress of the European Society of Cardiology, Birmingham, England, UK, Aug. 25–29, 1996 (Abstract P2367).
M.C. Sutter, Can. Med. Assoc. J., 152(5), pp. 667–670, Mar. 1, 1995.
Miettenen et al., European Heart Journal, vol. 17, pp. 682–688, 1996.
Science, vol. 272, Jun. 7, 1996.
(Abstract) J. Antimicrob. Chemother.; P.J. Cook et al.; *Chlamydia Pneumonia*: 1994 Dec.; 34(6): 859–73.
(Abstract Presse. Med.; P.J. Cook et al.; Clinical Aspects of *Chlamydia Pneumoniae* Infection; Feb. 4, 1995; 24(5): 278–82.
(Abstract) Br. J. Clin. Pract.; T.J. Blanchard et al.; Chlamydial Infections; Jul.–Aug. 1994; 48(4): 201–5.
Melnick et al.; The American Journal of Medicine: Past Infection by *Chlamydia pneumoniae* Strain TWAR and Asymptomatic Carotid Atherosclerosis; vol. 95, No. 1993, pp. 599–504.
P. Patel, et al.; BMJ; Association of *Helicobacter pylori* and *Chlamydia pneumoniae* infections with coronary heart disease and cardiovascular risk factors; Vo. 311, Sep. 15, 1995, pp. 711–714.
The Times Newspaper, Jun. 17, 1996.
Hospital Doctor, Jul. 18, 1996.
The Daily Mail Newspaper, Jun. 7, 1996.
New Scientist, Jun. 8, 1996.
The Independent on Sunday, Sep. 15, 1996.
SCRIP, Jun. 1996.

* cited by examiner

METHOD OF TREATMENT OF HEART DISEASE CAUSED BY *CHLAMYDIA PNEUMONIAE*

This application is a Continuation of international application No. PCT/GB97/02862 filed Oct. 17, 1997; which itself is a continuation-in-part U.S. prov. application No. 60/028,693 filed Oct. 18, 1996.

FIELD OF THE INVENTION

This invention relates to the treatment of heart disease, more particularly to the use of certain antibiotics in combatting atheroscelorsis.

DESCRIPTION OF THE PRIOR ART

Coronary heart disease is the largest single cause of premature death in the western world, and in the UK alone is responsible for about 160,000 deaths annually. The traditional view held by a significant proportion of the medical profession is that age and social and economic factors are the predominant causes of heart disease. In recent years, however, there has been a significant number of reports implicating certain bacteria in coronary heart disease, although these have met with considerable scepticism in some quarters.

Bacteria referred in such reports include *Helicobacter pylori* and *Chlamydia pneumoniae*. Thus, for example. Finnish researchers in the late 1980s reported that coronary heart disease sufferers were more likely to have high levels of antibodies to the *Chlamydia pneumoniae* bacterium than healthy people (The Lancet, 1988: 983–986). More recently, the organism itself has been found in atherosclerotic arteries of patients undergoing abdominal aortic aneurysm repair (J. Clin. Pathol., 1996, 49(2): 102–106). In the Journal of the American College of Cardiology, June 1996, 27(7): 1555–61, it was reported that 79% of patients undergoing surgery to excise atherosclerotic plaques showed an antibody to *Chlamydia pneumoniae* active in the lesions, but that only 4% of non-atherosclerotic pathology specimens showed the same antibody. It was alleged on this basis that the bacterium may be specifically linked with atheroma and not with other causes of arterial damage.

Other workers have reported similar findings, and it has been suggested that inflammation associated with persistent bacterial infection of arterial walls could trigger an immune reaction which raises fibrinogen and tissue factor levels in the blood and increases the potential for atherothrombosis.

However, there is still considerable scepticism about this theory within the medical profession, particularly amongst cardiologists, and many workers doubt whether *Chlamydia pneumoniae* is present in the diseased heart at all or, if it is, it is merely there as an innocent bystander. Thus, in the Journal of Infectious Diseases, 1996, 173(4): 957–62 it was reported that a research team had failed to culture *Chlamydia pneumoniae* from 58 samples of atheroma. Opinions are therefore firmly divided on the role, if any, of *Chlamydia pneumoniae* in heart disease.

The present invention is based on the unexpected finding that administration of certain antibiotics, more specifically macrolide antibiotics such as azithromycin, may lead to a reduction in markers of blood clotting and inflammation in the blood of post-myocardial infarction patients, possibly through eradication of underlying *Chlamydia pneumoniae* infection. Such administration of macrolide antibiotics may therefore be beneficial not only to cardiac patients, for example by reducing inflammation of heart tissue, blood clotting, susceptibility to angina, the likelihood of readmissions and/or need for bypass or other surgery, but also prophylatically to patients in general.

SUMMARY OF THE INVENTION

Thus viewed from one aspect the present invention provides a method of combatting atherosclerosis, said method comprising administering an effective amount of a macrolide antibiotic, for example an azalide, optionally together with one or more pharmaceutically acceptable carriers or excipients, to a subject.

In the method according to the invention, the macrolide antibiotic may if desired be administered with other useful agents such as platelet aggregation inhibitors, blood thinning agents, and/or lipid lowering agents. Thus in a further aspect, the present invention provides a composition for combatting atherosclerosis, the composition comprising a macrolide antibiotic or a derivative thereof, e.g. azithromycin together with one or more of the agents selected from the group consisting of platelet aggregation inhibitors, blood thinners, and/or lipid-lowering agents etc, optionally together with one or more carriers or excipients.

Viewed from a further aspect the present invention provides the use of a macrolide antibiotic e.g. azithromycin or a derivative thereof for the preparation of a composition for use in combatting atherosclerosis.

As is well known, macrolide antibiotics are characterised by the presence of a macrocyclic lactone ring to which one or more sugar molecules are attached. Representative examples of such antibiotics include erythromycin, spiramycin, oleandomycin, clarithromycin, dirithromycin, roxithromycin, josamycin, kitasamycin, midecamycin, miocamycin, rokitamycin, rosaramicin, azithromycin and derivatives thereof, e.g. salts such as phosphates and esters such as acetates.

Azithromycin [(2R, 3S, 4R, 5R, 8R, 10R, 11R, 12S, 13S, 14R)-13-(2,6-Dideoxy-3-C-3-O-dimethyl-α-L-ribohexopyranosyloxy)-2-ethyl-3,4,10-trihydroxy-3,5,6,8, 10,12,14-heptamethyl-11-(3,4,6-trideoxy-3-dimethylamino-β-D-xylohexopyranosyloxy)-1-oxa-6-azacyclopentadecan-15-one], available commercially in the dihydrate form as Zithromycin®, is a preferred macrolide or azalide antibiotic for use in accordance with the invention, having proved effective using single daily dosages over periods as short as three days. It will be appreciated that such simple dosage regimens are highly advantageous in securing patient compliance.

A typically daily dose of a macrolide antibiotic such as azithromycin will be 500 mg given orally, for example for up to 3 days, although other dosages and methods of administration may if desired by employed. It may be advantageous to administer a second course of the antibiotics some time, e.g. one, two or three months, after the first course in order to maximise the effect of the treatment. It may be even more advantageous to administer further courses of the antibiotic at intervals of one, two or three months after the second course in order to sustain the benefit. Typically this may be carried out for up to a year after the initial course has been administered.

The invention will now be described in a non-limiting manner by way of example:

EXAMPLE 1

A randomised double-blind study was conducted in which 60 male post-myocardial infarction patients were treated with azithromycin (500 mg per day, given orally for 3 days) or placebo. A further blinded course of azithromycin or placebo was given to 45 of the patients after a further 3 months. The results showed that azithromycin, particularly after double therapy, led to significant reduction in *Chlamydia pneumoniae* antibody titres (IgG) and to reduced levels of monocyte tissue factor, CDllb expression and serum markers of hypercoagulation and inflammation such as total leucocyte count and serum neopterin.

EXAMPLE 2

The relationship between antibodies against anti-*Chlamydia pneumoniae* (Cp) and future cardiovascular events in male survivors of myocardial infarction (MI) was explored. The effect of azithromycin antibiotic therapy was assessed in a subgroup of post-MI patients.

Between February 1995 and September 1995, 220 consecutive male patients attending a post-MI outpatient clinic at St George's Hospital, London were enrolled. Patients were screen for serum IgG antibodies against Cp by a microimmunofluorescence assay with elementary bodies of Cp strain IOL-207 as test antigen. Patients with chronic bronchitis, those currently taking macrolide antibiotics, and those with MI within the preceding 6 months (to ensure resolution of immune responses caused by infarction) were excluded. Also excluded were any subjects with serum that cross-reacted with *Chlamydia trachomatis* or *Chalmydia psitticai* antigens. Patients were stratified into one of three anti-Cp antibody titre groups: group Cp–ve (n=59), no detectable anti-Cp antibodies (seronegative); group Cp–I (n=74), seropositive at a serum dilution of between 1/8 and 1/32; and group Cp+ve (n=80), seropositive at a serum dilution of ≧1/64. Anti-Cp antibody titres were remeasured after 3 months in the latter group. Patients with Cp titre (≧1 in 64) on both occasions were entered in a double-blind placebo-controlled study of the effects of azithromycin therapy (either 500 mg/d for 3 days or two such courses 3 months apart) on anti-Cp titre and hemostatic and inflammatory markers in post-MI patients. These patients had their anti-Cp titre and other markers tested at 3 and at 6 months.

Adverse cardiovascular events (defined as the first admission to hospital with nonfatal MI; unstable angina requiring either intravenous anti-anginal therapy, coronary angioplasty, or urgent coronary artery bypass surgery; or cardiovascular death) were monitored for 18 months from the original Cp titre determination. The information was obtained from patients' clinic visits, telephone enquiries, case notes, and hospital computerised records.

Statistical Analysis

The frequency of adverse events was assessed in groups Cp–ve, Cp–I and Cp+ve. Additionally, Cp+ve patients were further divided into three subgroups: Cp+ve–NR, patients who did not enter the antibiotic study; Cp+ve–P, patients who were randomized to receive placebo medication; and Cp+ve–A, patients who were given either a single or double course of azithromycin.

The proportion of patients experiencing an adverse event was compared between group Cp–ve and all other groups by use of the $X^2$ test. The ORs for adverse cardiovascular events in each Cp+ve group relative to group Cp–ve were calculated by use of a multiple logistic regression model before and after adjustment for age, diabetes mellitus, hypertension, hyperlipidemia, smoking status (current, ever, or never) and previous coronary artery bypass surgery or percutaneous transluminal coronary angioplasty (STATA analysis). A value of $P<0.05$ was considered significant.

Results

Seven patients were excluded because their sera cross-reacted with other chlamydial species; analysis is hence based on the remaining 213 patients. Table 1 shows the baseline clinical characteristics. Patients with persisting seropositivity of ≧1/64 were randomized to either oral azithromycin (Cp+ve–A, 500 mg/d for 3 days [n=28] or 500 mg/d for 6 days [n=12]) or placebo (Cp+ve–P, n=20). Of the remaining 12 patients, 7 were unwilling to enter the trial, and 5 had other serious medical conditions that prevented their inclusion.

TABLE 1

Patient Characteristics and Incidence of Cardiovascular Events at a Mean of 18 ± 4 Months of Follow-up

| Group | Cp-ve (n = 59) | Cp-I (n = 74) | Cp + ve – NR (n = 20) | Cp + ve – P (n = 20) | Cp + ve – A (n = 40) |
|---|---|---|---|---|---|
| Age, y (mean ± D) | 63 ± 8 | 61 ± 9 | 63 ± 9 | 60 ± 9 | 58 ± 7 |
| Diabetes mellitus, n(%) | 6(10) | 9(12) | 6(30) | 8(40) | 12(30) |
| Hypertension, n(%) | 15(25) | 9(12) | 3(15) | 4(20) | 7(18) |
| Previous PTCA or CABG, n(%) | 12(20) | 20(27) | 8(40) | 6(30) | 12(30) |
| Hyperlipidemia, n(%) | 23(39) | 31(42) | 10(50) | 7(35) | 18(45) |
| Smoking (past), n(%) | 39(66) | 40(54) | 14(70) | 10(50) | 21(53) |
| Smoking (current), | 7(12) | 16(22) | 3(15) | 5(25) | 14(35) |

TABLE 1-continued

Patient Characteristics and Incidence of
Cardiovascular Events at a Mean of 18 ± 4 Months of
Follow-up

| Group | Cp-ve (n = 59) | Cp-I (n = 74) | Cp + ve – NR (n = 20) | Cp + ve – P (n = 20) | Cp + ve – A (n = 40) |
|---|---|---|---|---|---|
| n(%) | | | | | |
| Months since MI, mean ± SD | 44 ± 14 | 44 ± 27 | 46 ± 2 | 39 ± 24 | 47 ± 32 |
| Anterior MI, % | 53 | 53 | 50 | 58 | 53 |
| Ejection fraction, % | 41 ± 14 | 45 ± 13 | 41 ± 19 | 47 ± 14 | 48 ± 14 |
| Adverse cardiovascular events, n | | | | | |
| Death | 0 | 0 | 1 | 1 | 1 |
| Unstable angina/MI | 0 | 7 | 4 | 4 | 2 |
| PTCA/CABG | 4 | 4 | 1 | 0 | 0 |
| Total (%) | 4(7) | 11(15) | 6(30) | 5(25) | 3(*) |
| $x^2$ vs Cp-ve | | 2.1 | 7.3 | 4.9 | 0.9 |
| P | | .1 | .007 | .03 | NS |

Cp–ve indicates seronegative group of patients; Cp–I, group with intermediate antibody titres; Cp+ve–NR/P, group with elevated antibody titres either randomized to placebo or not randomized; Cp+ve–A, group with elevated antibody titres randomized to azithromycin; PTCA, percutaneous transluminal coronary angioplasty; and CABG, coronary artery bypass surgery.

At 6 months, in the patients participating in the antibiotic trial, anti-Cp titre fell to ≧1/16 in 43% of patients (17 of 40) receiving azithromycin compared with only 10% patients (2 of 20) taking placebo (P=0.02), The ORs for adverse cardiovascular events are shown for all groups in Table 2. The frequency of adverse events increased with rising anti-CP titre, which persisted after correction for confounding variables. Because there were no significant differences in cardiovascular risk factors or events between the Cp+ve–NR and Cp+ve–P groups, results of the two groups were combined in the calculation of the ORs. The rate of further cardiovascular events in the Cp+ve–A group was similar to that in the Cp–ve group (8% versus 7%; OR, 0.9; P=NS). Compared with patients in the combined placebo/nonrandomized group, the azithromycin-treated group had a fivefold reduction in cardiovascular events, with an OR of 0.2 (95% confidence interval, 0.05 to 0.8; P=0.03). There was no difference between the patients receiving either single or double azithromycin course in the proportion having a decrease in anti-Cp titre or the cardiovascular event rate.

TABLE 2

ORs for CV Events in Seronegative and
Seropositive Patient Groups

| Group | Total Cv Events, n (%) | Unadjusted OR (95% CI) | Adjusted OR (95% CI) |
|---|---|---|---|
| Cp-ve(n = 59) | 4(7) | | |
| Cp-I(n = 74) | 11(15) | 2.4(0.7–8.0) | 2.0(0.6–6.8) |
| Cp + VE-NR/P(n = 40) | 11(28) | 5.2(1.5–17.8)* | 4.2(1.2–15.5)\ |
| Cp + ve-A(n = 40) | 3(8) | 1.1(0.2–5.3) | 0.9(0.2–4.6) |

See Table 1 for explanation of group designations

Comparisons of cardiovascular (CV) events are for all groups relative to group Cp–ve (expressed as OR (95% confidence interval [CI]). Adjusted OR calculated after controlling for the following variables; age, diabetes mellitus, smoking status, hypertension, hyperlipidemia and previous coronary revascularization. *P=0.008, +0.03 vs group Cp–ve.

What is claimed is:

1. A method of treating atherosclerosis in a patient in need thereof, said method comprising administering an effective amount of azithromycin or a derivative thereof, optionally together with one or more pharmaceutically acceptable carriers or excipients, to a subject.

2. A method claimed in claim 1 wherein a second effective amount of azithromycin is administered about one, two or three months after administration of a first effective amount of azithromycin.

3. A method as claimed in claim 2 wherein one or more further effective amounts of azithromycin are added at intervals of one month or more.

4. The method of claim 2 wherein one or more further effective amounts of azithromycin are added at intervals of one, two or three months after a second effective amount of azithromycin.

* * * * *